US012607514B2

(12) United States Patent
Siegenthaler et al.

(10) Patent No.: US 12,607,514 B2
(45) Date of Patent: Apr. 21, 2026

(54) OPTICALLY CHARACTERIZING A TEXTILE FIBER STRUCTURE

(71) Applicant: Uster Technologies AG, Uster (CH)

(72) Inventors: Mario Siegenthaler, Herdern (CH); Ulf Schneider, Uster (CH)

(73) Assignee: Uster Technologies, AG, Uster (CH)

( * ) Notice: Subject to any disclaimer, the term of this patent is extended or adjusted under 35 U.S.C. 154(b) by 207 days.

(21) Appl. No.: 18/686,703

(22) PCT Filed: May 10, 2022

(86) PCT No.: PCT/CH2022/000008
§ 371 (c)(1),
(2) Date: Feb. 26, 2024

(87) PCT Pub. No.: WO2023/060367
PCT Pub. Date: Apr. 20, 2023

(65) Prior Publication Data
US 2024/0377257 A1 Nov. 14, 2024

(30) Foreign Application Priority Data

Oct. 12, 2021 (CH) ................................. 70379/2021

(51) Int. Cl.
*G01J 3/50* (2006.01)
*D06H 3/02* (2006.01)
(Continued)

(52) U.S. Cl.
CPC .................. *G01J 3/50* (2013.01); *D06H 3/02* (2013.01); *G01N 33/36* (2013.01); *G01J 2003/467* (2013.01)

(58) Field of Classification Search
CPC ...... G01J 3/50; G01J 3/46; G01J 3/462; G01J 2003/467; D06H 3/02; G01N 33/36;
(Continued)

(56) References Cited

U.S. PATENT DOCUMENTS 5,684,583 A * 11/1997 Abe ................... G01N 15/1456
356/336
6,452,157 B1 9/2002 Hosel
(Continued)

FOREIGN PATENT DOCUMENTS

EP 3321668 A2 5/2018

OTHER PUBLICATIONS

Engels Guido "Impurities Detecting Device in the Fibres Pre Treatment Step", Dec. 15, 2021, EP 3371351 B1 (Year: 2021).*
(Continued)

*Primary Examiner* — Sang H Nguyen
(74) *Attorney, Agent, or Firm* — TechnicalAttorney; Rick Barnes

(57) ABSTRACT

The invention relates to a computer-implemented method for optically characterizing a textile fiber structure. A plurality of pieces of information on the color at different locations of the textile fiber structure are detected by an optical sensor system. The detected color information is transmitted to a computer (107) and is entered into a color space (2) in the form of a scatter plot (31) by the computer. A frequency density distribution (4) of the scatter plot (31) is determined, and the frequency density distribution (4) is numerically specified. The invention allows a change in the material of the textile fiber structure to be ascertained and optimizes the elimination of foreign materials from the textile fiber structure.

26 Claims, 4 Drawing Sheets

(51) Int. Cl.
   *G01J 3/46* (2006.01)
   *G01N 33/36* (2006.01)
(58) Field of Classification Search
   CPC ............ G01N 33/362; G01N 15/1433; G01N
                  15/1456; G01N 2021/8592; G01N
                  2021/8444; G01N 2021/8887; G01N
                  21/8915; G01N 2015/1402; D01G
                  31/006; D01G 31/003; D01G 23/08
   See application file for complete search history.

(56) References Cited

U.S. PATENT DOCUMENTS

| | | | | |
|---|---|---|---|---|
| 6,633,383 | B1 * | 10/2003 | Jackson | G01N 21/8915 |
| | | | | 356/238.2 |
| 6,741,726 | B1 * | 5/2004 | Nevel | G01N 33/367 |
| | | | | 356/429 |
| 6,848,149 | B1 * | 2/2005 | Baechler | D01G 31/003 |
| | | | | 19/65 R |
| 7,155,356 | B2 * | 12/2006 | Mantyla | G01N 21/8922 |
| | | | | 702/183 |
| 10,192,100 | B2 * | 1/2019 | Valvik | G06V 20/698 |

| | | | | |
|---|---|---|---|---|
| 2004/0156044 | A1 * | 8/2004 | Pirani | G01N 33/365 |
| | | | | 356/238.3 |
| 2005/0078306 | A1 * | 4/2005 | Engels | G01N 21/94 |
| | | | | 356/238.3 |
| 2009/0002707 | A1 * | 1/2009 | Berger | G01N 21/8915 |
| | | | | 73/160 |
| 2011/0031393 | A1 * | 2/2011 | Goebel | G01N 21/64 |
| | | | | 356/326 |
| 2011/0249255 | A1 * | 10/2011 | Bentien | G01N 15/1459 |
| | | | | 356/51 |
| 2014/0293091 | A1 * | 10/2014 | Rhoads | A61B 5/6898 |
| | | | | 348/234 |
| 2018/0047208 | A1 * | 2/2018 | Marin | H04N 13/257 |
| 2022/0275542 | A1 | 9/2022 | Schneider et al. | |

OTHER PUBLICATIONS

Lu et al "A Hand-held Cotton Colour Measuring Instrument With Wireless Transmission Function", Mar. 12, 2014, CN 203479397 ( Year: 2014).*

Kirstein Kay-Uwe et al "Determining the Hairiness Lengths On a Yarn", Jun. 12, 2014 (Year: 2014).*

\* cited by examiner

OPTICALLY CHARACTERIZING A TEXTILE FIBER STRUCTURE

FIELD OF THE INVENTION

The present invention is in the field of yarn manufacturing. It relates to a computer-implemented method and a device for the optical characterization of a textile fiber structure, according to the independent patent claims. It can be used, for example, but not exclusively, in the blow room of a spinning mill.

DESCRIPTION OF THE PRIOR ART

Textile fibers are usually delivered to a spinning mill in the form of fiber bales. There, the textile fiber bales are placed in a continuous row, often intentionally combining textile fiber bales of different types and/or qualities into a single laydown in order to obtain a corresponding fiber blend. The laydown is removed layer by layer using a bale opener. The removed textile fibers are pneumatically transported in the form of fiber flocks in a stream of air to various cleaning stages, which break down the fiber flocks more finely and remove foreign materials from them.

U.S. Pat. No. 6,452,157 B1 relates to a device on a fiber processing device for detecting and processing impurities, foreign substances and fibers in textile fiber material. The device has at least two light sources which alternately illuminate the fiber material with different colors. In addition, a sensor is provided that receives the colors of the light reflected by the fiber material. If the color of the fiber material changes abruptly from a predetermined color, an electrical signal is generated. A multicolor light source with more than two colors is used to enable the luminous colors to be adapted depending on the application, e.g. to different or changing colors of the fiber material. The type of colors of the multicolor light source can be selected depending on the color of the fiber material to be illuminated.

In a method for optimizing a yarn manufacturing process according to WO-2021/051210 A1, foreign materials in a textile fiber structure are monitored. The textile fiber structure is irradiated with electromagnetic radiation from at least two color ranges. The foreign materials are classified into different color classes according to their colors. If a sufficiently large sample with classified foreign materials is available, a frequency distribution of the foreign materials is determined for the color classes and compared with a reference frequency distribution. If the determined frequency distribution deviates from the reference frequency distribution, at least one of a number of optimization actions is performed, e.g., a warning signal is issued.

EP-3'321'68 A2 discloses a method for evaluating the quality of a yarn. The yarn is exposed to polychromatic, preferably white, light. A measurement signal representing the red, green and blue color components of the light reflected by the yarn is detected. The red, green and blue color components are transformed into an evaluation color space in which measurement points of the measurement signal are described by a first and a second coordinate, which represent the color, and by a third coordinate, which represents the brightness. The quality of the yarn is evaluated using the first, second and third coordinates of the measurement points in the evaluation color space. This makes it possible to distinguish foreign substances from diameter deviations of the yarn. Black foreign fibers can also be detected.

However, it is not only foreign materials that are a problem in the spinning mill, but also the basic textile material itself. It happens again and again that this changes unintentionally over time during production. Such material changes can have various causes, e.g., an incorrect composition of the laydown or a change in quality within a lot of textile fiber bales. In contrast to the occurrence of a foreign material, they do not occur abruptly, but continuously over a longer period of several minutes or hours. The material changes are reflected in undesirable quality changes in the yarn produced and ultimately also in the final textile products.

SUMMARY OF THE INVENTION

It is an object of the present invention to provide a method and a device for the optical characterization of a textile fiber structure. The invention is intended to avoid undesirable changes in the quality of the textile fiber structure and the textile end products produced therefrom. In particular, it is intended to detect large quantities of material that have mistakenly entered the textile fiber structure and unintentional changes to the laydown. The resulting material changes occur continuously within a longer period of several minutes or hours. The present invention is therefore not primarily interested in individual events in the textile fiber structure, such as the presence of a single foreign material, but in the medium and long-term composition of the textile fiber structure. A further object of the invention is to optimize the elimination of foreign materials from the textile fiber structure.

These and other objects are solved by the computer-implemented method according to the invention and the device according to the invention, as defined in the independent patent claims. Advantageous embodiments are given in the dependent patent claims.

The computer-implemented method according to the invention is used for the optical characterization of a textile fiber structure. In this process, a plurality of pieces of information on color is detected by an optical sensor system at different locations of the textile fiber structure. The captured color information is transmitted from the optical sensor system to a computer, where it is received and stored. The stored color information is entered by the computer in a color space in the form of a scatter plot. A frequency density distribution of the scatter plot is determined by the computer. The frequency density distribution is specified numerically by the computer. A signal dependent on the numerical specification is output by the computer.

The color information is preferably recorded on a sample basis.

The color space is, for example, a one- or two-dimensional color space in which information about brightness is not taken into account.

According to one embodiment, the computer defines a characteristic region in the color space based on the frequency density distribution. For the numerical specification of the frequency density distribution, the characteristic region is specified numerically. For this purpose, the computer can use, for example, a length, an area or a volume of the characteristic region, a geometric shape of the characteristic region and/or a course of a boundary line or a boundary surface that delimits the characteristic region.

In a first application example, a change in the numerical specification of the frequency density distribution is used by the computer to infer a change in a material composition of the textile fiber structure, and the signal output by the computer is dependent on the change in the material composition. The signal output by the computer is preferably used to trigger at least one of the following actions: outputting a graphic to an operator, outputting a warning to an operator, outputting a recommended action to an operator, shutting down at least one processing machine, changing a setting on at least one processing machine. The computer can be given a threshold value and/or a tolerance range, the exceeding of which indicates a change in the numerical specification of the frequency density distribution by a parameter of the numerical specification.

In a second application example, the computer recognizes a foreign material in the textile fiber structure on the basis of the numerical specification of the frequency density distribution, and the signal output by the computer controls a separation of the recognized foreign material from the textile fiber structure. An element of the scatter plot can be recognized by the computer as belonging to a foreign material if the element in question lies outside the characteristic region. According to a first alternative, the computer suspends the separation of foreign materials until a statistically representative characteristic region is present and numerically specified. According to a second alternative, the computer is specified an initial characteristic region, and the characteristic region is continuously adapted by the computer to a material composition of the textile fiber structure.

According to one embodiment, the computer corrects the color information, a threshold value and/or a tolerance range with a degree of dissolution which indicates the extent to which the textile fiber structure is dissolved into individual fiber flocks. For this purpose, for example, at least one image of the textile fiber structure is recorded by the optical sensor system and the image area onto which fiber material is imaged is determined by the computer from the at least one image by image processing; the computer determines a mass flow of the textile fiber structure per time unit; the computer calculates the degree of dissolution as a scalar quantity by forming a quotient from the image area onto which fiber material is imaged on the one hand and from the mass flow on the other hand. The degree of dissolution is preferably determined by the computer according to the formula $$X = A_F/(A_T \cdot m),$$

wherein $A_F$ is the image area onto which the fiber material is imaged, $A_T$ is the total area of the image and m is the mass flow of the textile fiber structure per unit time.

The device according to the invention is used for the optical characterization of a textile fiber structure. It contains an optical sensor system for detecting a plurality of pieces of information on color at different locations of the textile fiber structure and a computer connected to the optical sensor system. The optical sensor system comprises transmitting means for transmitting the detected color information to the computer. The computer comprises receiving means for receiving the color information transmitted by the optical sensor system. The computer is adapted to enter the captured color information in a color space as a scatter plot, to determine a frequency density distribution of the scatter plot and to specify the frequency density distribution numerically and to output a signal dependent on the numerical specification.

The color space is, for example, a one- or two-dimensional color space in which information about brightness is not taken into account.

According to one embodiment, the computer is adapted to define a characteristic region in the color space based on the frequency density distribution and to numerically specify the characteristic region for the numerical specification of the frequency density distribution.

In a first application example, the computer is adapted to infer a change in a material composition of the textile fiber structure from a change in the numerical specification of the frequency density distribution, and the signal output by the computer is dependent on the change in the material composition. The computer is adapted in such a way that the signal output by it is suitable for triggering at least one of the following actions: outputting a graphic to an operator, outputting a warning to an operator, outputting a recommendation for action to an operator, switching off at least one processing machine, changing a setting on at least one processing machine.

In a second application example, the device additionally comprises a separation unit connected to the computer. The computer is adapted to recognize foreign materials in the textile fiber structure on the basis of the numerical specification of the frequency density distribution and, when the foreign material is recognized, to control a separation of the recognized foreign material by the separation unit by means of the signal output by it. The computer can be adapted to recognize an element of the scatter plot as belonging to a foreign material if the element in question lies outside the characteristic region. According to a first alternative, the computer is adapted to suspend the separation of the foreign materials until a statistically representative characteristic region is present and numerically specified. According to a second alternative, the computer is adapted to store an initial characteristic region and to continuously adapt the stored characteristic region to a material composition of the textile fiber structure.

According to one embodiment, the computer is adapted to additionally determine a degree of dissolution of the textile fiber structure, which indicates the extent to which the textile fiber structure is dissolved into individual fiber flocks, and to correct the color information, a threshold value and/or a tolerance range with the degree of dissolution. For this purpose, the optical sensor system can comprise an image sensor for recording at least one image of the textile fiber structure; the computer can be adapted to determine from the at least one image the image area onto which fiber material is imaged by image processing, to determine a mass flow of the textile fiber structure per time unit and to calculate the degree of dissolution as a scalar quantity by forming a quotient from the image area onto which fiber material is imaged on the one hand and from the mass flow on the other hand. The computer is preferably adapted to determine the degree of dissolution according to the formula $$X = A_F/(A_T \cdot m),$$

wherein $A_F$ is the area of the image onto which the fiber material is imaged, $A_T$ is the total area of the image and m is the mass flow of the textile fiber structure per unit time.

The optical characterization of the textile fiber structure according to the invention offers several advantages. For example, a change in the numerical specification of the frequency density distribution can be used to infer a change in the material composition of the textile fiber structure. It is important for a spinning mill to detect such a material change at an early stage, as it can indicate a faulty composition of the laydown. If it is detected at an early stage of the spinning process, e.g. at a fiber cleaner in the blow room, the production of yarn from the wrong textile fiber material can be prevented in good time by making the appropriate correction.

Furthermore, the invention optimizes the separation of foreign materials from the textile fiber structure. Based on the characterization according to the invention, a boundary adapted to the currently processed textile fiber structure can be drawn between the base material of the textile fiber structure and foreign materials to be separated out and used for separating out the foreign materials. This ensures that, on the one hand, the foreign materials are reliably separated out and, on the other hand, as little good material as possible is wasted from the textile fiber structure.

Overall, the invention prevents undesirable changes in the quality of the textile fiber structure and the textile end products made from it.

In the present document, terms such as "textile fiber material" or the like always refer to the base material of which the textile fiber structure consists for the most part. Any impurities present due to individual foreign materials do not play a direct role in the present invention and are not to be taken into account when referring to "composition of the textile fiber material", "changes in the textile fiber material", "material changes" or the like.

BRIEF DESCRIPTION OF THE DRAWINGS

In the following, an embodiment of the invention is explained in detail with reference to the schematic drawings.

DETAILED DESCRIPTION OF THE PREFERRED EMBODIMENT

Figure 1:
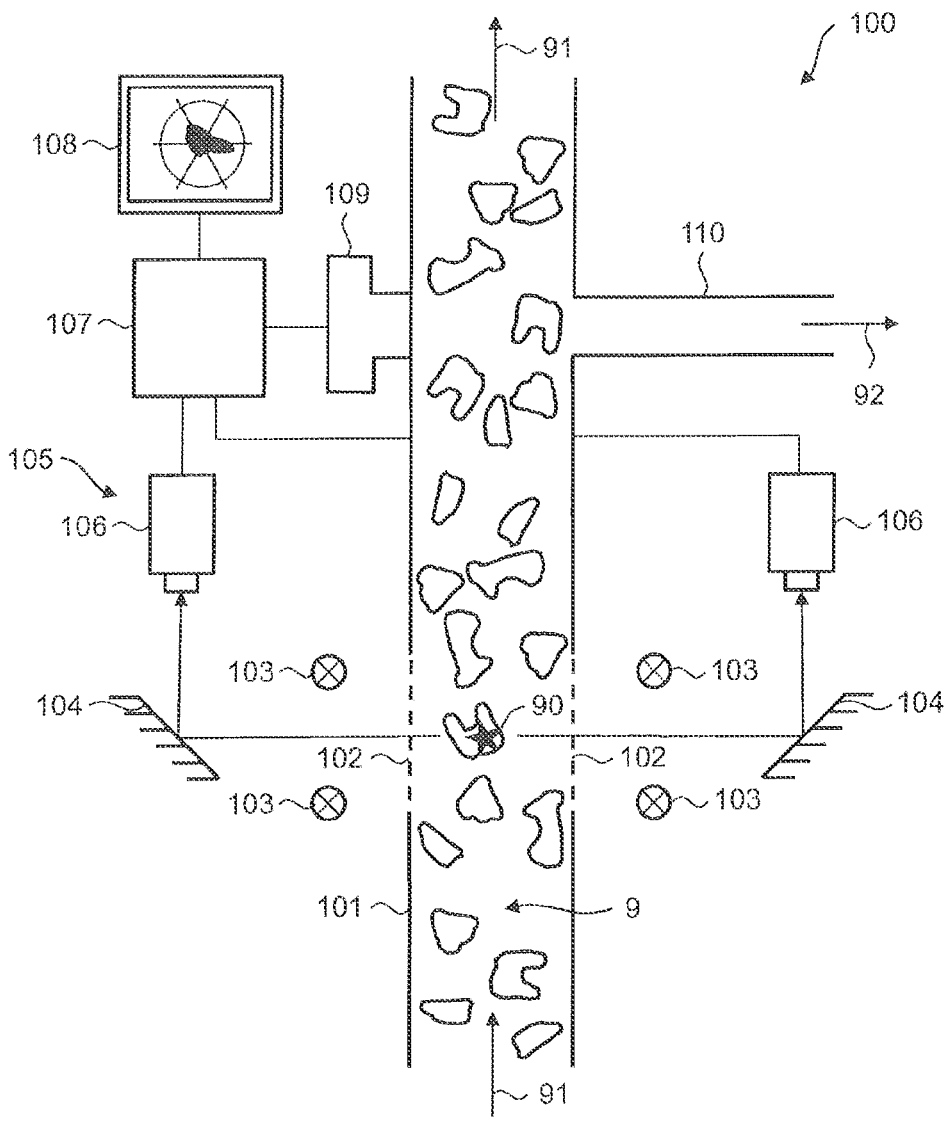
FIG. 1 shows an embodiment of the device according to the invention.

FIG. 1 schematically illustrates an embodiment of the device 100 according to the invention using the example of a fiber cleaner in a blow room. The device 100 is used for the automatic optical characterization of a textile fiber structure 9, which in the present example is a fiber flock stream, for example a cotton flock stream. It contains a pneumatic fiber transport channel 101 for pneumatically transporting the fiber flock stream 9 in an air flow. The transport direction of the fiber flock stream 9 and the air stream is indicated by arrows 91 in FIG. 1.

Four light sources 103, e.g., fluorescent tubes or LED arrays, are arranged near windows 102 in a wall of the fiber transport channel 101. The light sources 103 illuminate the fiber flock stream 9 in the fiber transport channel 101 from different directions.

An optical sensor system 105 is arranged on the fiber transport channel 101. It records color information about the fiber flock stream 9. In the embodiment shown in FIG. 1, the sensor system 105 contains two cameras 106 that record images of the fiber flock stream 9 through the windows 102 from two different directions. The light emitted by the light sources 103 is deflected to the cameras 106 by means of correspondingly tilted mirrors 104 after interacting with the fiber flock stream 9. The cameras 106 are equipped, for example, with CMOS or CCD photosensors whose pixels are covered with mosaic color filters in the arrangement of a Bayer matrix. The output signals of such photosensors can be interpolated inside or outside the cameras 106 by means of algorithms known per se in such a way that each pixel or image segment is assigned a color in a color model.

The cameras 106 are connected to a computer 107 for automatic evaluation of output signals from the optical sensor system 105. The computer 107 is adapted to enter the captured color information in a color space as a scatter plot, to determine a frequency density distribution of the scatter plot and to specify the frequency density distribution numerically (see FIG. 2 below).

The computer 107 is connected to an output unit 108. A signal output from the computer 107 can cause an output of a result of the characterization, for example a graphic, on the output unit 108. The output unit 108 can be, for example, a computer screen or a printer. In one embodiment, it is designed as a touch screen and thus serves as an input and output unit.

A separation unit 109 is arranged on the fiber transport channel 101 downstream of the sensor system 105 (with respect to the transport direction 91). The separation unit 109 is used for selective separation of foreign materials 90 from the fiber flock stream 9. Such a separation unit 109 is known per se, for example from WO2006/079426-A1. In a preferred embodiment, it contains a plurality of pressurized air nozzles which can be controlled individually or in groups by a signal output by the computer 107. If the sensor system 105 detects an unacceptable foreign material 90 in the fiber flock stream 9, the relevant air nozzle of the separation unit 109 is caused by the signal output by the computer 107 to blow out compressed air perpendicular to the transport direction 91 when the foreign material 90 has arrived at the level of the separation unit 109. As a result, the foreign material 90 is blown into a separation channel 110, which is arranged from the fiber transport channel 101 in a separation direction 92 that is substantially perpendicular to the transport direction 91. The uncontaminated fiber flocks, on the other hand, continue on their way with the fiber flock stream 9 in order to be processed further.

The separation unit 109 can be controlled by the computer 107 and/or directly by the sensor system 105. In the latter case, each camera 106 can be assigned a computer, for example in the form of a microprocessor, and the cameras 106 can be connected directly to the separation unit 109 and output their signals to it. Such direct connections are not shown in FIG. 1 for the sake of simplicity. In a further alternative, the separation unit 109 is controlled by a computer which is assigned to the separation unit 109 itself.

Figures 2A, 2B:
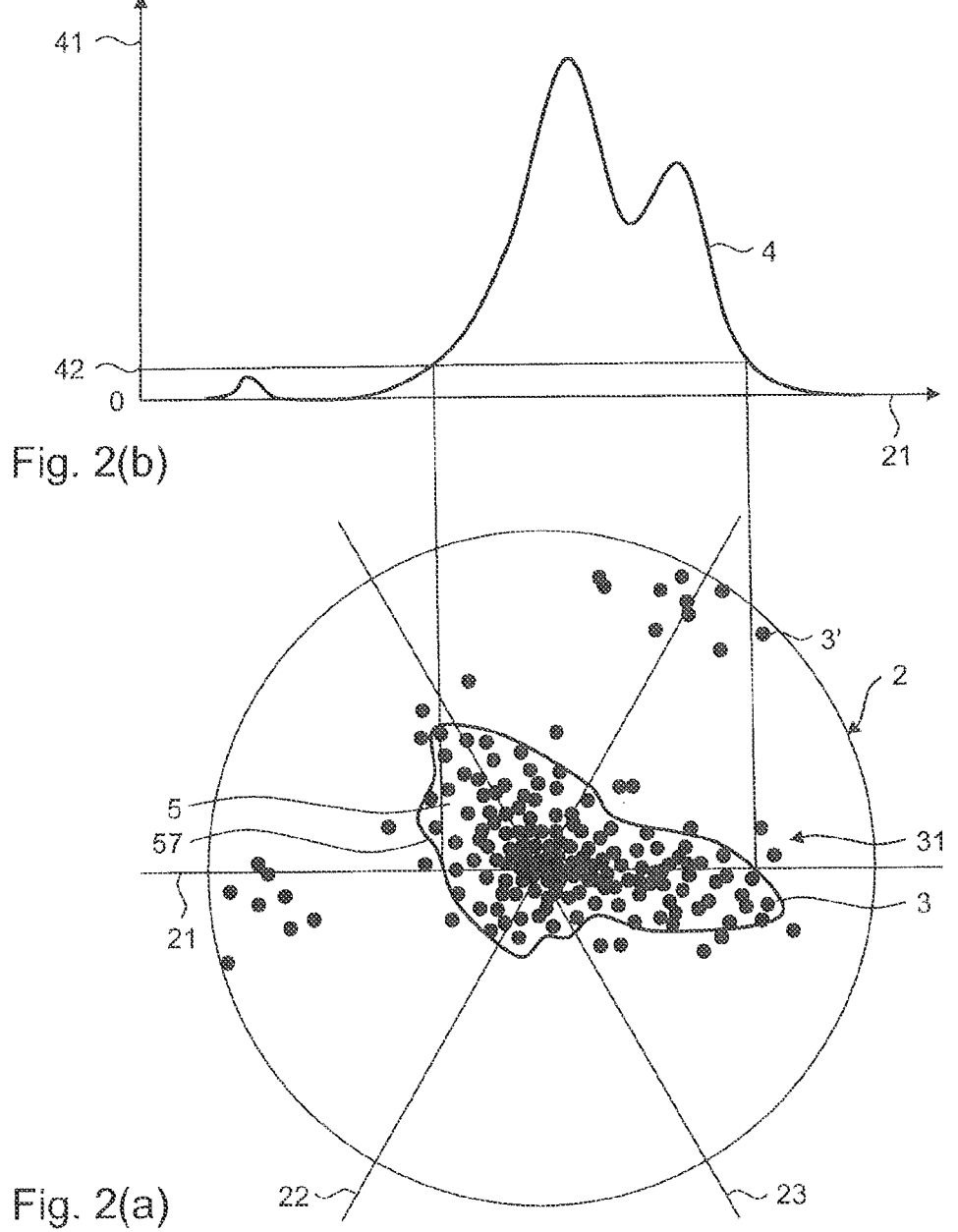
FIG. 2(a) shows a two-dimensional color space with a scatter plot and a characteristic region.
FIG. 2(b) shows a one-dimensional frequency density distribution of the scatter plot of FIG. 2(a).

FIG. 2(a) schematically shows a two-dimensional color space 2. This color space 2 provides information about the hue and color saturation, but not about the brightness. It can, for example, be a horizontal sectional plane through the known HSV color space; in polar coordinates, the angle corresponds to the hue (H) and the radius to the color saturation(S). Instead of such a perception-oriented color model, however, a technical-physical color model is preferred for the present invention. An advantageous color space 2 is, for example, the I1I2I3 color space without brightness component (I1).

According to the invention, a plurality of pieces of color information about different locations of the textile fiber structure 9 is detected by the optical sensor system 105, preferably on a sample basis. A random sample may comprise color information from multiple locations of a single image and/or color information from different images. Preferably, it comprises a plurality of color information from several pixels of several digital images. The images do not necessarily have to be taken in immediate succession; for example, one image per second may suffice, while the image frequency is much higher. The sample should contain such a large number of elements that it is statistically representative of the textile fiber structure 9. With knowledge of the invention, the person skilled in the art is able to determine the required minimum size of the sample.

The detected color information is sent from the sensor system 105 to the computer 107, received and stored by the computer 107. The stored color information is entered by the computer 107 in a color space, e.g., in the two-dimensional color space 2 of FIG. 2($a$), as color events 3 represented by dots in a scatter plot 31. The representation of the scatter plot 31 can be output as a graphic to an operator on the output unit 108 on the basis of the signal output by the computer 107, but this is optional; alternatively, the color information can be entered purely virtually in the computer 107.

The computer 107 then determines a frequency density distribution of the scatter plot 31. Since the color information is discrete measured values, the frequency density distribution determined in this way will have steps. It can, but need not, be approximated mathematically by a continuous function; corresponding calculation methods are known. An exemplary one-dimensional frequency density distribution 4 approximated as continuous along an axis 21 of the color space 2 of FIG. 2($a$) is shown schematically in FIG. 2($b$), wherein the vertical axis 41 indicates the frequency density. The frequency density distribution 4 is determined not only in one dimension (as shown in FIG. 2($b$) for the sake of simplicity), but in the entire two-dimensional color space 2 of FIG. 2($a$). For approximately white cotton, the frequency density is greatest in the vicinity of a gray or white point 24 (see FIG. 3) lying in the coordinate origin of the color space 2, but the maximum need not lie on the gray point 24, because each cotton has its characteristic coloration. The present invention is concerned with the automatic characterization of this coloration.

According to the invention, the frequency density distribution 4 is specified numerically by the computer 107. Thanks to their basic training in mathematics, the person skilled in the art knows how a curve or a surface can be specified numerically: e.g., by its extreme values, saddle points, gradients at certain points in certain directions, approximation by a suitable fit function, etc. In the following, without limiting the generality, a certain type of numerical specification of the frequency density distribution 4 is discussed by way of example, which is particularly suitable for textile fiber structures 9.

Based on the frequency density distribution 4, the computer 107 defines a characteristic region 5 in the color space 2. The characteristic region 5 need not be contiguous. In the simplest case, the characteristic region 5 is delimited by a boundary line 57 with a constant frequency density 42. The corresponding frequency density 42 is selected so that a large proportion, e.g., 95% or 99%, of the scatter plot 31 lies within the characteristic region 5. The color events 3' outside the characteristic region 5 are then outliers that are not considered characteristic of the textile fiber structure 9 and are therefore not taken into account. Such outliers 3' can, for example, be caused by incorrect measurements or represent foreign materials 90 that are undesirably present in the textile fiber structure 9.

The boundary line 57 does not necessarily have to be defined by a constant frequency density 42. It can be defined, for example, by maintaining a constant safety distance from a line with constant frequency density 42 so that it lies further out in the color space 2. Alternatively, it can be created, for example, by stretching the radii belonging to a line with constant frequency density 42 with a constant stretch factor. However, all such possibilities for defining the characteristic region 5 must use the frequency density distribution 4 as a basis.

Figure 3A:
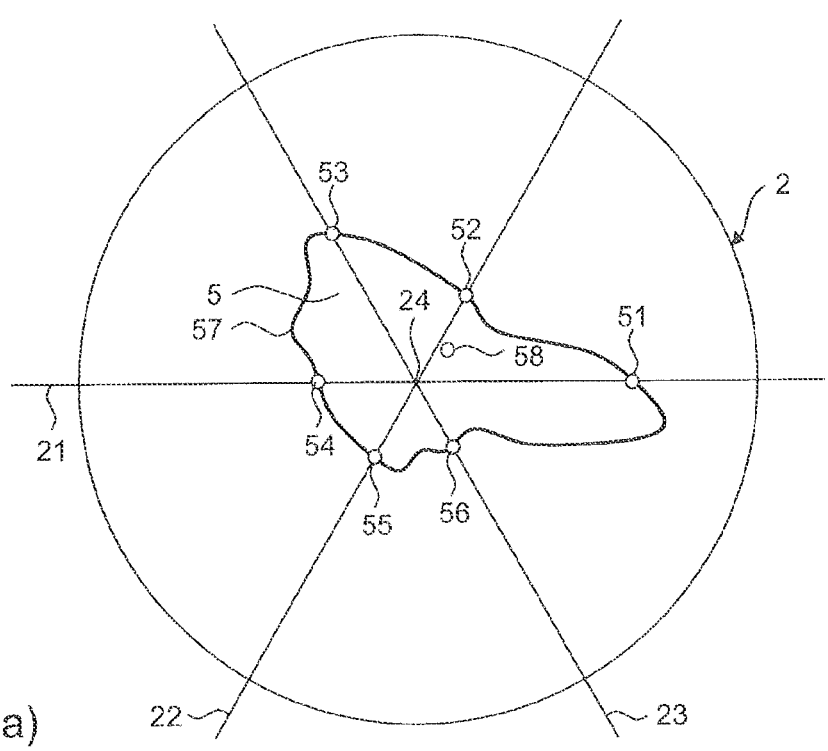
FIG. 3 shows a two-dimensional color space with a characteristic region, wherein the characteristic regions of FIGS. 3(a) and 3(b) differ from each other.
Figure 3B:
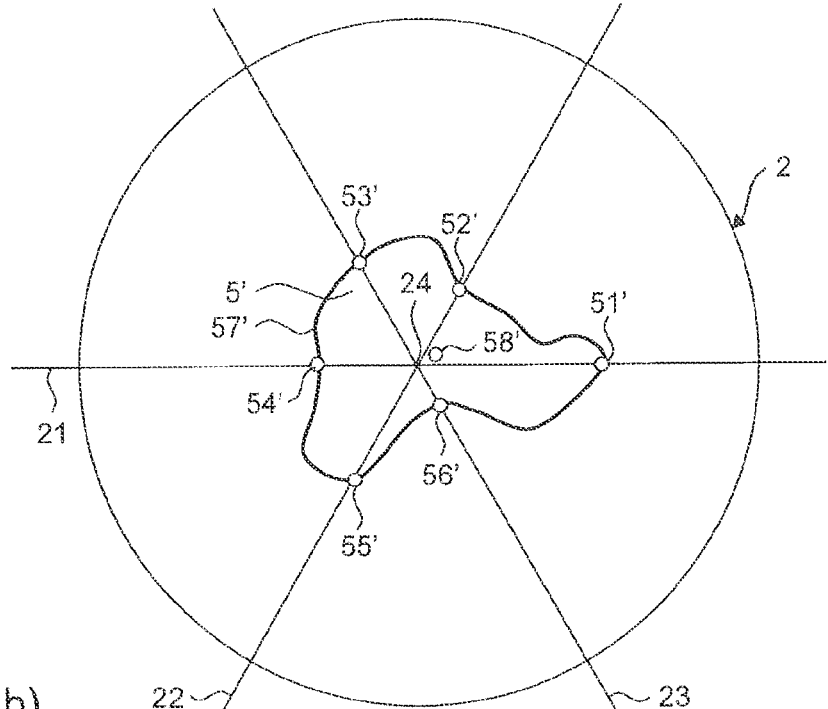

The characteristic region 5 is in turn specified numerically by the computer 107, which is illustrated by way of example in FIG. 3 ($a$). The numerical specification may, for example, take into account the following properties of the characteristic region 5:

a length, an area or a volume of the characteristic region 5, depending on whether the region 5 is one-, two- or three-dimensional, a geometric shape of the characteristic region 5, in two dimensions, e.g., a position of a center of area 58 or a center of contour of the area 5, and/or a course of a boundary line 57 or a boundary surface that delimits the characteristic region 5. The numerical specification can be carried out using interpolation points. In FIG. 3 ($a$), for example, six interpolation points 51-56 are drawn, which lie in pairs on axes 21-23, which intersect at the coordinate origin (gray point 24) and have an angular distance of 60° from each other. In this example, each interpolation point 51-56 is uniquely determined by its radial distance from the coordinate origin. For numerical specification, the distance values associated with the interpolation points 51-56 can be specified individually or mathematically linked to form a single value.

Two preferred application examples for the method according to the invention and the device 100 according to the invention are described below.

A first application example aims to detect a change in the textile fiber material or its composition over time and automatically trigger a corresponding action, e.g., issue a warning signal. Thanks to the warning signal, an incorrect composition of the bale laydown can be detected, for example.

Figure 4:
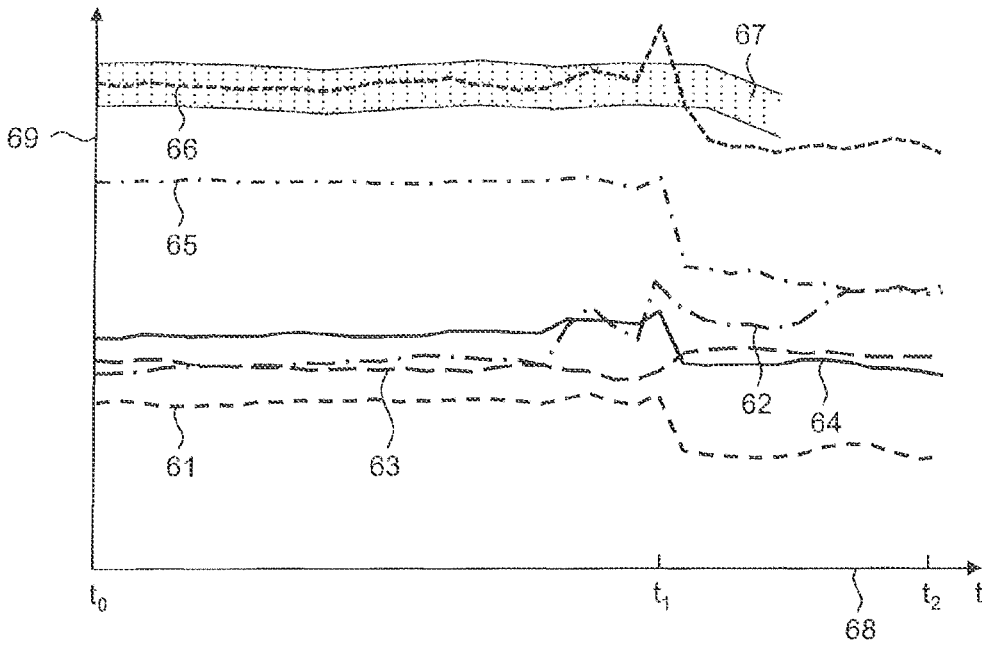
FIG. 4 shows temporal progressions of values that numerically specify a characteristic region.

FIG. 4 illustrates an embodiment of the first application example. Therein, values of the radial components of the six interpolation points 51-56 of FIG. 3 are plotted along a vertical axis 69 versus time t along a horizontal time axis 68 as curves 61-66. Each curve 61-66 represents the time course of a color component lying on the corresponding axis 21-23 (FIG. 3), e.g., green 61, cyan 62, blue 63, red 64, magenta 65 and yellow 66. Normally, it is sufficient to record the values periodically at larger time intervals, e.g. every 15 minutes, so that the diagram of FIG. 4 covers a period of several hours.

In the example in FIG. 4, the values change only insignificantly in the first few hours and are therefore within a tolerance range. However, at a certain point in time $t_1$ they begin to change noticeably. This can be an indication of an incorrect composition of the laydown. The material change can be determined by the computer 107 using a single value in FIG. 4 and/or by linking the values. For this purpose, tolerance ranges can be specified, for example, and the computer 107 outputs a signal if these are exceeded. The current values or running average values from several consecutively recorded values can be taken into account. In FIG. 4, a tolerance range 67 is indicated for the yellow curve 66 in the form of a band initially surrounding the curve 66. The tolerance range 67 is preferably tracked to a running mean value of the curve 66 in order to compensate for a drift that is not caused by a change in material. Around the time $t_1$, the curve 66 leaves the tolerance range 67, which results in the output of the signal.

The signal output by the computer 107 can, for example, automatically trigger at least one of the following actions: outputting a graphic to an operator, outputting a warning to an operator, outputting a recommendation for action to an operator, shutting down at least one processing machine, changing a setting on at least one processing machine.

FIG. 3 illustrates how the characteristic region 5 can change over time as shown in FIG. 4. FIG. 3 (a) shows an example of a characteristic region 5 at an initial time $t_0$, while FIG. 3 (b) shows a modified characteristic region 5' at a later time $t_2 > t_1 > t_0$. The shape of the characteristic region 5 has visibly changed in the time interval $[t_0, t_2]$, which is quantitatively recorded by the numerical specification described above. The characteristic region 5' at the later time $t_2$ has different interpolation points 51'-56' (see also FIG. 4), a different boundary line 57', a different center of gravity 58', a different area, etc. than the characteristic region 5 at the initial time $t_0$.

A second application example relates to the separation of foreign materials 90 from the textile fiber structure 9 (see FIG. 1). The characteristic region 5 with its color events 3 is characteristic of the textile fiber structure 9, while all color events 3' outside the area 5 are regarded as foreign materials 90 that are to be separated out. In order to avoid false separations, the characteristic region 5 should be adapted to the respective processed textile fiber structure 9.

According to a first alternative, the separation of foreign material can be suspended during a learning phase at the beginning of the processing of a new lot of textile fiber material. The color information about the textile fiber structure 9 is recorded and stored until a statistically representative characteristic region 5 is present and numerically specified. As soon as this is the case, the foreign material separation is activated. It causes all color events 3' outside the characteristic region 5 to be eliminated from the textile fiber structure 9 as foreign materials 90. The separation takes place by means of the separation unit 109, which is controlled by a signal output by the computer 107. This first alternative has the disadvantage that during the learning phase the textile fiber structure 9 enters the subsequent process steps uncleaned. However, the learning phase is so short compared to the total processing time of the lot that the improved separation of foreign material due to the invention by far outweighs the disadvantage.

According to a second alternative, foreign materials 90 are separated from the outset. To make this possible, an initial characteristic region 5 is specified before processing begins. This can, for example, be a characteristic region determined for a previously processed textile fiber material, determined by a simple color measurement on the textile fiber material to be processed or designed on the basis of theoretical considerations. During processing, the initial characteristic region 5 can then be continuously adapted to the current textile fiber material by the computer 107. The separation is again carried out by means of the separation unit 109, which is controlled by a signal output by the computer 107.

In both alternatives, the expected or current ejection rate, i.e., the number of ejections per time unit or per unit of mass of the textile fiber structure 9, can be output by the computer 107 on the output unit 108 (FIG. 1) to an operator. The operator can be given the option of confirming or changing the output separation rate via the input unit 108. A change in the separation rate can consist of a reduction or an increase of the same. In the former case, the characteristic region 5 (FIG. 2(a)) is enlarged, in the latter case it is reduced. Thanks to the already existing numerical specification of the frequency density distribution 4 (FIG. 2(b)), such a targeted change can be carried out quickly and easily by the computer 107 automatically.

Figure 5:
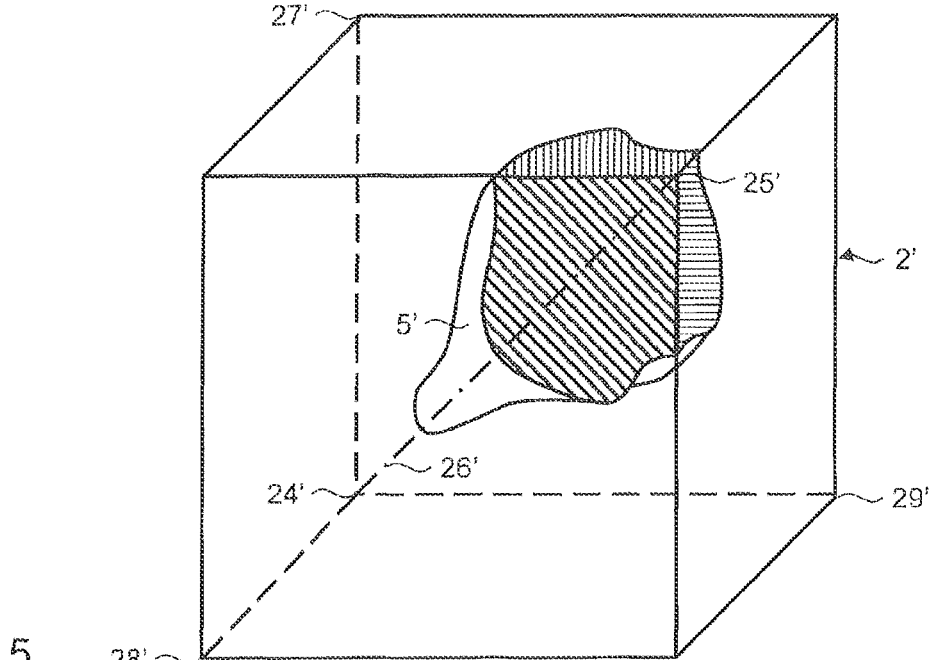
FIG. 5 shows a three-dimensional RGB color space with a characteristic region.

FIG. 5 illustrates that not only two-dimensional but also, for example, three-dimensional color spaces can be used in the method according to the invention. It shows the known three-dimensional RGB color space 2' with a black point 24', a white point 25', a red point 27', a green point 28' and a blue point 29'. A characteristic region 5' is schematically drawn in the RGB color space 2' in accordance with the method according to the invention. In this case, the three-dimensional characteristic region 5' is based on a frequency density distribution of a three-dimensional scatter plot, which is not shown in FIG. 5 for the sake of clarity. For almost white cotton, the frequency density is highest in the vicinity of a gray value axis 26' (spatial diagonal connecting the black point 24' with the white point 25').

While the two-dimensional color information according to FIGS. 2(a) and 3 is not influenced by the brightness, at least in the ideal case, the three-dimensional color information according to FIG. 5 does contain the brightness. However, in a device 100 according to FIG. 1, the measured brightness is influenced by the dissolution of the textile fiber structure 9 into individual fiber flocks: The better the textile fiber structure 9 is dissolved into individual fiber flocks, the greater the brightness, and vice versa. It can therefore be advantageous, particularly in the color space 2' of FIG. 5, to correct the color information with a degree of dissolution that indicates the extent to which the textile fiber structure 9 is dissolved into individual fiber flocks.

The degree of dissolution and its determination are discussed in detail in WO-2017/117688 A1. Preferably, the degree of dissolution is calculated as a scalar quantity by forming a quotient from the image area $A_F$ of an image recorded by the camera 106 onto which fiber material is imaged, on the one hand, and from the mass flow m of the fiber flock stream 9, on the other hand. An exemplary definition of the degree of dissolution X is as follows:

$$X = A_F/(A_T \cdot m),$$

wherein $A_F$ is the image area, $A_T$ is the total area of the image and m is the mass flow of the fiber flock stream 9 per time unit. In this example, smaller values of X indicate a lower, poorer dissolution of the fiber flock stream 9, while larger values indicate a higher, better dissolution.

The color information can be corrected with the degree of dissolution X using a theoretical formula or empirically determined correction values, which can be stored in a table, for example. Instead of or in addition to the color information, a threshold value and/or a tolerance range can be corrected with the degree of dissolution X. The correction with the degree of dissolution X may be useful not only in three-dimensional color spaces 2', but also in two-dimensional color spaces 2. The correction is carried out by the computer 107.

It is understood that the present invention is not limited to the embodiments discussed above. With knowledge of the invention, the person skilled in the art will be able to derive further variants which also form part of the subject matter of the present invention.

In the above description, the invention is discussed using examples with two-dimensional color spaces 2 (FIGS. 2(*a*) and 3) and three-dimensional color spaces 2' (FIG. 5). The person skilled in the art is also able to adapt the present invention to a one-dimensional color space.

Likewise, the person skilled in the art is able to generalize the invention from the color spaces 2, 2' in the visible range of the electromagnetic spectrum discussed here to color spaces which comprise the spectral ranges adjacent to the visible range, ultraviolet and infrared, or parts thereof.

In the above description, the invention is discussed with reference to the example of a fiber cleaner in a blow room, wherein the textile fiber structure 9 is pneumatically transported through the device 100 (FIG. 1) in the form of a fiber flock stream. However, the invention is not limited to this application. It can also be used, for example, in spinning preparation, where the textile fiber structure is in the form of a sliver, or in the spinning/winding department, where the textile fiber structure is in the form of yarn.

LIST OF REFERENCE SIGNS

100 Device according to the invention
101 Fiber transport channel
102 Window in the wall of the fiber transport channel
103 Light sources
104 Mirror
105 Sensor system
106 Cameras
107 Computer
108 Output and input unit
109 Separation unit
110 Separation channel
2, 2' Color space
21-23 Axis of the color space
24 Grey point
24' Black point
25 White point
26' Gray value axis
27' Red point
28' Green point
29' Blue point
3 Color events
3 Outliers
31 Scatter plot
4 Frequency density distribution
41 Frequency density axis
5, 5' Characteristic region
51-56, 51'-56' Interpolation points
57, 57' Boundary line
58, 58' Center of gravity
61-66 Curves showing the time progression of color components
67 Tolerance range
68 Time axis
69 Vertical diagram axis
9 Fiber flock flow
90 Foreign material
91 Transport direction of the fiber flock flow
92 Separation direction

The invention claimed is:

1. Computer-implemented method for the optical characterization of a textile fiber structure (9), wherein
   a plurality of pieces of information on color is detected by an optical sensor system (105) at different locations of the textile fiber structure (9),
   the captured color information is transmitted from the optical sensor system (105) to a computer (107) connected to the optical sensor system, where it is received and stored by the computer,
   the stored color information is entered by the computer (107) in a color space (2, 2') in the form of a scatter plot (31),
   a frequency density distribution (4) of the scatter plot (31) is determined by the computer (107),
   the frequency density distribution (4) is specified numerically by the computer (107), and
   a signal dependent on the numerical specification is output by the computer (107).

2. Method according to claim 1, wherein the color space (2) is a one- or two-dimensional color space in which information about a brightness is not taken into account.

3. Method according to claim 1, wherein a characteristic region (5, 5') in the color space (2, 2') is defined by the computer (107) on the basis of the frequency density distribution (4) and the characteristic region (5, 5') is specified numerically for the numerical specification of the frequency density distribution (4).

4. Method according to claim 3, wherein a length, an area or a volume of the characteristic region (5, 5'), a geometric shape of the characteristic region (5, 5') and/or a course of a boundary line (57) or a boundary surface which delimits the characteristic region (5, 5') is used by the computer (107) for the numerical specification of the characteristic region (5, 5').

5. Method according to the claim 3, wherein an element of the scatter plot (31) is recognized by the computer (107) as belonging to a foreign material (90) if the element in question lies outside the characteristic region (5, 5').

6. Method according to claim 1, wherein a change in a material composition of the textile fiber structure (9) is inferred by the computer (107) from a change in the numerical specification of the frequency density distribution (4), and the signal output by the computer (107) is dependent on the change in the material composition.

7. Method according to claim 6, wherein the signal output by the computer (107) is used to trigger at least one of the following actions: outputting a graphic to an operator, outputting a warning to an operator, outputting a recommended action to an operator, shutting down at least one processing machine, changing a setting on at least one processing machine.

8. Method according to claim 6, wherein the computer (107) is given a threshold value and/or a tolerance range (67), the exceeding of which indicates a change in the numerical specification of the frequency density distribution (4) by a parameter of the numerical specification.

9. Method according to claim 1, wherein the computer (107) recognizes a foreign material (90) in the textile fiber structure (9) on the basis of the numerical specification of the frequency density distribution (4), and the signal output by the computer controls a separation of the recognized foreign material (90) from the textile fiber structure (9).

10. Method according to claim 9, wherein the computer (107) suspends the separation of the foreign materials (90) until a statistically representative characteristic region (5, 5') is present and numerically specified.

11. Method according to claim 9, wherein an initial characteristic region (5, 5') is specified to the computer (107) and the characteristic region (5, 5') is continuously adapted by the computer (107) to a material composition of the textile fiber structure (9).

12. Method according to claim 1, wherein the computer (107) corrects the color information, a threshold value and/or a tolerance range with a degree of dissolution which indicates the extent to which the textile fiber structure (9) is dissolved into individual fiber flocks.

13. Method according to claim 12, wherein at least one image of the textile fiber structure (9) is recorded by the optical sensor system (105) and the image area onto which fiber material is imaged is determined by the computer from the at least one image by image processing, the computer (107) determines a mass flow of the textile fiber structure (9) per time unit, and the computer (107) calculates the degree of dissolution as a scalar quantity by forming a quotient from the image area onto which the fiber material is imaged on the one hand and from the mass flow on the other hand.

14. Method according to claim 12, wherein the computer (107) determines the degree of dissolution according to the formula $$X = A_F/(A_T \cdot m),$$

wherein $A_F$ is the image area onto which fiber material is imaged, $A_T$ is a total area of the image and m is a mass flow of the textile fiber structure (9) per unit time.

15. Device (100) for the optical characterization of a textile fiber structure (9), with an optical sensor system (105) for detecting a plurality of pieces of information on color at different locations of the textile fiber structure (9), and a computer (107) connected to the optical sensor system (105), wherein the optical sensor system (105) adapted to transmitting the detected color information to the computer (107), the computer (107) adapted to receive the color information transmitted by the optical sensor system (105), and the computer (107) is adapted to enter the captured color information in a color space (2, 2') as a scatter plot (31), to determine a frequency density distribution (4) of the scatter plot (31), to specify the frequency density distribution (4) numerically and to output a signal dependent on the numerical specification.

16. Device according to claim 15, wherein the color space (2) is a one- or two-dimensional color space in which information about a brightness is not taken into account.

17. Device (100) according to claim 15, wherein the computer (107) is adapted to define a characteristic region (5, 5') in the color space (2, 2') based on the frequency density distribution (4) and to numerically specify the characteristic region (5, 5') for the numerical specification of the frequency density distribution (4).

18. Device (100) according to claim 17, wherein the computer (107) is adapted to recognize an element of the scatter plot (31) as belonging to a foreign material (90) if the element in question lies outside the characteristic region (5, 5').

19. Device (100) according to claim 15, wherein the computer (107) is adapted to infer a change in a material composition of the textile fiber structure (9) from a change in the numerical specification of the frequency density distribution (4), and the signal output by the computer (107) is dependent on the change in the material composition.

20. Device (100) according to claim 19, wherein the computer (107) is adapted in such a way that the signal output by it is suitable for triggering at least one of the following actions: outputting a graphic to an operator, outputting a warning to an operator, outputting a recommendation for action to an operator, switching off at least one processing machine, changing a setting on at least one processing machine.

21. Device (100) according to claim 15, wherein the device (100) additionally comprises a separation unit (109) connected to the computer (107), and the computer (107) is adapted to recognize a foreign material (90) in the textile fiber structure (9) on the basis of the numerical specification of the frequency density distribution (4) and, when the foreign material (90) is recognized, to control a separation of the recognized foreign material (90) by the separation unit (109) by means of the signal output by it.

22. Device (100) according to claim 21, wherein the computer (107) is adapted to suspend the separation of the foreign materials (90) until a statistically representative characteristic region (5, 5') is present and numerically specified.

23. Device (100) according to claim 21, wherein the computer (107) is adapted to store an initial characteristic region (5, 5') and to continuously adapt the stored characteristic region (5, 5') to a material composition of the textile fiber structure (9).

24. Device (100) according to claim 15, wherein the computer (107) is adapted to additionally determine a degree of dissolution of the textile fiber structure (9), which indicates the extent to which the textile fiber structure (9) is dissolved into individual fiber flocks, and to correct the color information, a threshold value and/or a tolerance range with the degree of dissolution.

25. Device (100) according to claim 24, wherein the optical sensor system (105) includes an image sensor (106) for recording at least one image of the textile fiber structure (9), and the computer (107) is adapted to determine from the at least one image the image area onto which the fiber material is imaged by image processing, to determine a mass flow of the textile fiber structure (9) per time unit, and to calculate the degree of dissolution as a scalar quantity by forming a quotient from the image area onto which the fiber material is imaged on the one hand and from the mass flow on the other.

26. Device (100) according to claim 25, wherein the computer (107) is adapted to determine the degree of dissolution according to the formula $$X = A_F/(A_T \cdot m),$$

wherein $A_F$ is the area of the image onto which the fiber material is imaged, $A_T$ is the total area of the image and m is the mass flow of the textile fiber structure (9) per unit time.

* * * * *